US012784884B2

(12) United States Patent
Bechtel et al.

(10) Patent No.: US 12,784,884 B2
(45) Date of Patent: *Nov. 3, 2026

(54) PATIENT SAFETY USING VIRTUAL OBSERVATION

(71) Applicant: Cerner Innovation, Inc., Kansas City, MO (US)

(72) Inventors: Todd Bechtel, Overland Park, KS (US); Lisa Schaberg, Lee's Summit, MO (US); Julie Hull, Kansas City, MO (US); Michelle Padgett, Leawood, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 59 days.

This patent is subject to a terminal disclaimer.

(21) Appl. No.: 19/026,280

(22) Filed: Jan. 16, 2025

(65) Prior Publication Data

US 2025/0201363 A1 Jun. 19, 2025

Related U.S. Application Data

(63) Continuation of application No. 18/916,575, filed on Oct. 15, 2024, now Pat. No. 12,676,219, which is a continuation of application No. 16/731,274, filed on Dec. 31, 2019, now Pat. No. 12,148,512.

(51) Int. Cl.

*G16H 10/60* (2018.01)
*G16H 40/60* (2018.01)
*G16H 50/30* (2018.01)

(52) U.S. Cl.

CPC ............ *G16H 10/60* (2018.01); *G16H 40/60* (2018.01); *G16H 50/30* (2018.01)

(58) Field of Classification Search

CPC ......... G16H 10/60; G16H 50/30; G16H 40/60

See application file for complete search history.

(56) References Cited

U.S. PATENT DOCUMENTS

| | | | | |
|---|---|---|---|---|
| 9,368,014 B1 * | 6/2016 | Bittman | ................. | G08B 25/08 |
| 2015/0221202 A1 * | 8/2015 | Russell | ................. | A61B 5/1117 340/573.7 |
| 2015/0363567 A1 * | 12/2015 | Pettus | .................... | G16H 50/30 705/3 |
| 2017/0147770 A1 * | 5/2017 | Xu | ....................... | A61B 5/7275 |

* cited by examiner

*Primary Examiner* — Steven G.S. Sanghera

(74) *Attorney, Agent, or Firm* — Invoke

(57) ABSTRACT

Methods, systems, and computer-readable media are provided for improving patient safety using virtual observation. A falls risk assessment and a patient safety risk assessment are initially provided within an electronic health record of a patient. A clinician is prompted at a clinician device to provide input to the falls risk assessment and the patient safety risk assessment for the patient. Based on the input, a safety assessment score is determined for the patient. The safety assessment score is provided to the clinician via the clinician device and the clinician is prompted to initiate an order to place a camera in the room of the patient. Based on the order, a virtual sitter may be assigned to the patient to monitor the camera.

20 Claims, 10 Drawing Sheets

400

PATIENT SAFETY USING VIRTUAL OBSERVATION

INCORPORATION BY REFERENCE; DISCLAIMER

Each of the following applications are hereby incorporated by reference: application Ser. No. 18/916,575 filed on Oct. 15, 2024; application Ser. No. 16/731,274 filed on Dec. 31, 2019. The applicant hereby rescinds any disclaimer of claims scope in the parent application(s) or the prosecution history thereof and advises the USPTO that the claims in the application may be broader than any claim in the parent application(s).

BACKGROUND

Medical facilities, such as hospitals, face many challenges in addition to simply caring for patients. In order to meet these challenges, fiscal responsibility is paramount. Continued surveillance and avoidance of "never events" like falls prevention remains a key factor in cost containment.

According to recent studies, falls are a leading cause of death among people over the age of 65 and 10% of the fatal falls for patients over 65 years of age occur in a hospital setting. Of these hospital-based falls, approximately 30% will result in a serious injury with the cost to care for these injuries estimated to reach $54.9 billion per year by 2020. Patients fall for a variety of reasons, including not calling for nursing assistance, the bed exit alarm not being set, patients being on high risk medications, and delays in communication when the nurse is called. Findings suggest that attention to optimizing patient care delivery results in a reduction in the occurrence of adverse events.

In some instances, patients require one-on-one monitoring to redirect risky behavior or address a patient's immediate needs that may otherwise result in falls. One-on-one monitoring allows for observing a change in a patient's condition quickly and accurately. However, such one-on-one monitoring is costly, decreases time caregivers can spend providing care, and results in dissatisfaction among staff.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to systems and methods for providing improved safe patient care using virtual observation. More particularly, embodiments of the present disclosure utilize a virtual observation solution to enable trained observation technicians to monitor multiple patient rooms from a central monitoring station, reduce sitter labor costs, and prevent falls and other adverse events. To do so, a falls risk assessment and a patient safety risk assessment are initially provided within an electronic health record of a patient. A clinician is prompted at a clinician device to provide input to the falls risk assessment and the patient safety risk assessment for the patient. Based on the input, a safety assessment score is determined for the patient. The safety assessment score is provided to the clinician via the clinician device and the clinician is prompted to initiate an order to place a sitter at the bedside or place a camera in the room of the patient. Based on the order, a virtual sitter may be assigned to the patient to monitor the camera.

In some embodiments, the virtual sitter is prompted to provide documentation for the patient at a virtual observation interface. Upon receiving documentation from the virtual sitter device corresponding to patient behavior, the clinician determines whether to continue or discontinue the virtual sitter for the patient.

In some embodiments, virtual guardrails are assigned for the patient. The virtual guardrails may be three-dimensional (3D) zones positions around a patient bed or chair, safety zones to detect tampering with invasive line or tube placement, safety zones for staff safety, patient elopement zones that provide a wide angle of a patient room to detect elopement or visitor monitoring zones to prevent drug diversion and abuse.

BRIEF DESCRIPTION OF THE SEVERAL VIEWS OF THE DRAWING

The description references the attached drawing figures, wherein.

DETAILED DESCRIPTION

Figure 1:
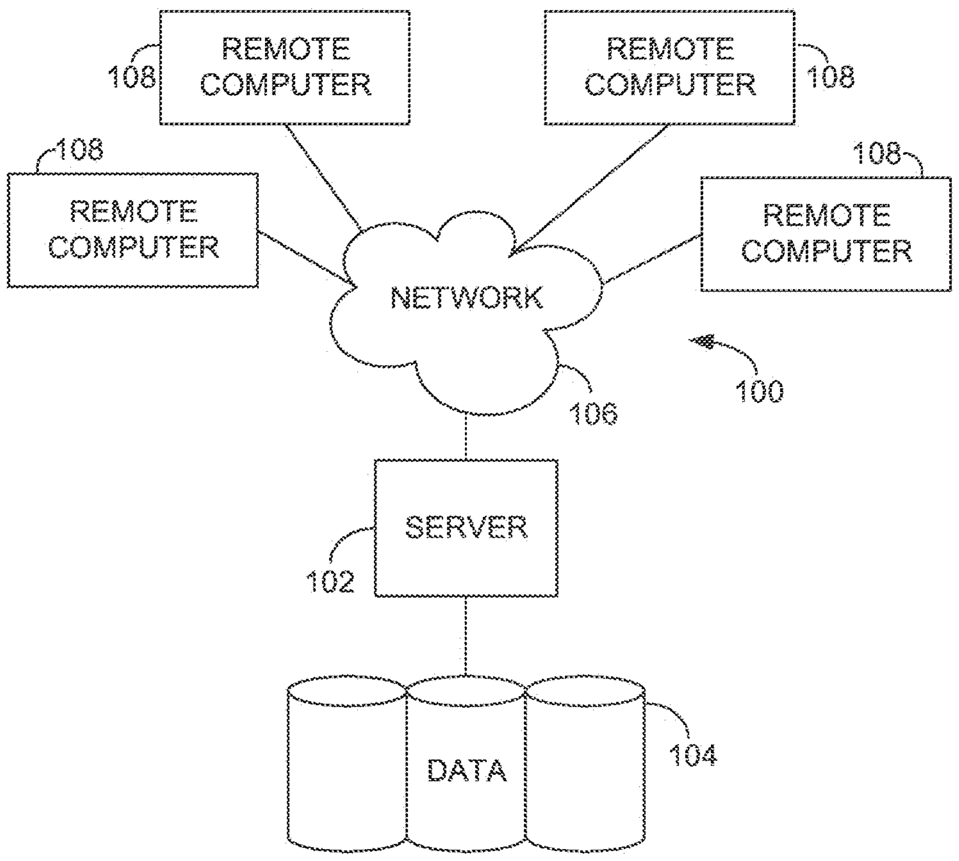
FIG. 1 is a block diagram of an exemplary operating environment suitable to implement embodiments of the present disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

As noted in the Background, medical facilities, such as hospitals, face many challenges in addition to simply caring for patients. In order to meet these challenges, fiscal responsibility is paramount. Continued surveillance and avoidance of "never events" like falls prevention remains a key factor in cost containment.

According to recent studies, falls are a leading cause of death among people over the age of 65 and 10% of the fatal falls for patients over 65 years of age occur in a hospital setting. Of these hospital-based falls, approximately 30% will result in a serious injury with the cost to care for these injuries estimated to reach $54.9 billion per year by 2020. Patients fall for a variety of reasons, including not calling for nursing assistance, the bed exit alarm not being set, patients being on high risk medications, and delays in communication when the nurse is called. "Findings suggest that attention to optimizing patient care delivery results in a reduction in the occurrence of adverse In some instances, patients require one-on-one monitoring to redirect risky behavior or address a patient's immediate needs that may otherwise result in falls. One-on-one monitoring allows for observing a change in a patient's condition quickly and accurately. However, such one-on-one monitoring is costly, decreases time caregivers can spend providing care, and results in dissatisfaction among staff.

Embodiments of the present disclosure relate to systems and methods for providing improved patient safety using virtual observation. More particularly, embodiments of the present disclosure utilize a virtual observation solution to enable trained observation technicians to monitor multiple patient rooms from a central monitoring station, reduce sitter labor costs, and prevent falls and other adverse events. To do so, a falls risk assessment and a patient safety risk assessment are initially provided within an electronic health record of a patient. A clinician is prompted at a clinician device to provide input to the falls risk assessment and the patient safety risk assessment for the patient. Based on the input, a safety assessment score is determined for the patient. The safety assessment score is provided to the clinician via the clinician device and the clinician is prompted to initiate an order to place a sitter at the bedside or place a camera in the room of the patient. Based on the order, a virtual sitter may be assigned to the patient to monitor the camera.

In some embodiments, the virtual sitter is prompted to provide documentation for the patient at a virtual observation interface. Upon receiving documentation from the virtual sitter device corresponding to patient behavior, the clinician determines whether to continue or discontinue the virtual sitter for the patient.

In some embodiments, virtual guardrails are assigned for the patient. The virtual guardrails may be 3D zones positions around a patient bed or chair, safety zones to detect tampering with invasive line or tube placement, safety zones for staff safety, patient elopement zones that provide a wide angle of a patient room to detect elopement, or visitor monitoring zones to prevent drug diversion and abuse.

Embodiments of the present invention maximize time caregivers can spend providing care at the bedside. This results in greater caregiver satisfaction and improves retention of staff. Moreover, occurrence of "never events" can be significantly reduced or avoided, altogether.

Embodiments of the present invention provide a virtual solution that uses 3D cameras to track patient movement and alert centralized monitoring staff if patients move beyond bed or room zones, need assistance, or interfere with lines or medical devices. The solution allows virtual monitoring technicians to communicate with patients and share patient assistance alerts with their assigned care team members via a mobile device (e.g., Zebra® TC51). Integration between the EHR and the mobile device facilitates care team assignments and ensures alerts and communications are routed to the appropriate care team members. The integration between the virtual sitter technology and the communication devices work in concert with each other. For example, when virtual sitters identify a patient at risk for falling, they can notify that patient's nurse and/or the appropriate care team easily and quickly with the touch of a single button. All documentation generated or utilized by the virtual observation system is integrated with the EHR of the patient.

In embodiments, the virtual observation system enables one virtual sitter to observe up to twelve patients, allows more primary care technicians to be available on the floor to assist nurses with day-to-day activities, which in turn allows nurses and/or the appropriate care team to spend more with patients. The virtual observation system drives the algorithms and the communications to the care team based on patient care assignments. A central monitoring station is staffed with virtual sitters, and assignment-based alerts and communications are pushed to the correct care team members. An end-user device team is available to assist with camera management.

In some embodiments, machine learning algorithms are employed to learn which patients are identified and selected for virtual observation. Data and information may be captured over time and the machine learning algorithms can be trained to predict or suggest when a patient is similar to another patient that has been previously assigned a virtual sitter. Additionally or alternatively, the machine learning algorithms can be trained to determine when a falls risk assessment and a patient safety risk assessment should be provided within an electronic health record of a patient, when a virtual sitter should prompted to provide documentation for the patient at a virtual observation interface, or when the clinician should be prompted to determine whether to continue or discontinue the virtual sitter for the patient. The machine learning algorithms may also be trained to predict where the virtual guardrails should be positioned by the virtual sitter (i.e., based on similarities to other patients).

Although described with respect to falls risk and patient safety risk, embodiments of the present invention may additionally benefit patients under seizure watch or behavioral health and general safety concerns within a controlled environment. In each of these settings, embodiments of the present invention could reduce the required physical presence and improve the patient experience.

Accordingly, one embodiment of the present disclosure is directed to a system. The system includes a processor; and a computer storage medium storing computer-usable instructions that, when used by the processor, cause the processor to: provide a falls risk assessment and a patient safety risk assessment within an electronic health record of a patient; prompt a clinician at a clinician device to provide input to the falls risk assessment and the patient safety risk assessment for the patient; based on the input, determine a safety assessment score for the patient; provide the safety assessment score of the patient to the clinician via the clinician device prompt the clinician to initiate an order to place a camera in the room of the patient; and based on the order, assign a virtual sitter to the patient.

In another embodiment, the present disclosure directed to a computerized method. The method includes providing a falls risk assessment and a patient safety risk assessment within an electronic health record of a patient. The method also includes prompting a clinician at a clinician device to provide input to the falls risk assessment and the patient safety risk assessment for the patient. The method further includes, based on the input, determining a safety assessment score for the patient. The method also includes providing the safety assessment score of the patient to the clinician via the clinician device. The method further includes prompting the clinician to initiate an order to place a camera in the room of the patient. The method also includes, based on the order, assigning a virtual sitter to the patient. The method further includes prompting the virtual sitter to provide documentation for the patient at a virtual observation interface. The method also includes, upon receiving documentation from the virtual sitter device corresponding to patient behavior, prompting the clinician to determine whether to continue or discontinue the virtual sitter for the patient.

In yet another embodiment, the present disclosure is directed to one or more computer storage media having computer-executable instructions embodied thereon that, when executed by a computer, causes the computer to perform operations. The operations include providing a falls risk assessment and a patient safety risk assessment within an electronic health record of a patient. The operations also include prompting a clinician at a clinician device to provide input to the falls risk assessment and the patient safety risk assessment for the patient. The operations further includes, based on the input, determining a safety assessment score for the patient. The operations also include providing the safety assessment score of the patient to the clinician via the clinician device. The operations further include prompting the clinician to initiate an order to place a camera in the room of the patient. The operations also include, based on the order, assigning a virtual sitter to the patient. The operations further include receiving an assignment of virtual guardrails for the patient. The virtual guardrails may include 3D zones positioned around a patient bed or chair, safety zones to detect tampering with invasive line or tube placement, safety zones for staff safety, patient elopement zones that provide a wide angle of a patient room to detect elopement, or visitor monitoring zones to prevent drug diversion and abuse.

Having briefly described embodiments of the present invention, an exemplary operating environment suitable for use in implementing embodiments of the present invention is described below. FIG. 1 provides an aspect of an example operating environment with which embodiments of the present invention may be implemented. The aspect of an operating environment is illustrated and designated generally as reference numeral 100.

Beginning with FIG. 1, an exemplary computing environment suitable for use in implementing embodiments of the present technology is shown. FIG. 1 is an exemplary computing environment (e.g., health-information computing-system environment) with which embodiments of the present technology may be implemented. The computing environment is illustrated and designated generally as reference numeral 100. The computing environment 100 is merely an example of one suitable computing environment and is not intended to suggest any limitation as to the scope of use or functionality of the present technology. Neither should the computing environment 100 be interpreted as having any dependency or requirement relating to any single component or combination of components illustrated therein. It will be appreciated by those having ordinary skill in the art that the connections illustrated in FIG. 1 are also exemplary as other methods, hardware, software, and devices for establishing a communications link between the components, devices, systems, and entities, as shown in FIG. 1, may be utilized in the implementation of the present technology. Although the connections are depicted using one or more solid lines, it will be understood by those having ordinary skill in the art that the exemplary connections of FIG. 1 may be hardwired or wireless, and may use intermediary components that have been omitted or not included in FIG. 1 for simplicity's sake. As such, the absence of components from FIG. 1 should not be interpreted as limiting the present technology to exclude additional components and combination(s) of components. Moreover, though devices and components are represented in FIG. 1 as singular devices and components, it will be appreciated that some embodiments may include a plurality of the devices and components such that FIG. 1 should not be considered as limiting the number of a device or component.

The present technology might be operational with numerous other special-purpose computing system environments or configurations. Examples of well-known computing systems, environments, and/or configurations that might be suitable for use with the present technology include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present technology may be operational and/or implemented across computing system environments such as a distributed or wireless "cloud" system. Cloud-based computing systems include a model of networked enterprise storage where data is stored in virtualized storage pools. The cloud-based networked enterprise storage may be public, private, or hosted by a third party, in embodiments. In some embodiments, computer programs or software (e.g., applications) are stored in the cloud and executed in the cloud. Generally, computing devices may access the cloud over a wireless network and any information stored in the cloud or computer programs run from the cloud. Accordingly, a cloud-based computing system may be distributed across multiple physical locations.

The present technology might be described in the context of computer-executable instructions, such as program modules, being executed by a computer. Exemplary program modules comprise routines, programs, objects, components, and data structures that perform particular tasks or implement particular abstract data types. The present technology might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including database 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer-readable media does not include signals per se.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations including operating systems, device drivers and the like. The remote computers might also be physically located in traditional and nontraditional clinical environments so that the entire medical community might be capable of integration on the network. The remote computers might be personal computers, servers, routers, network PCs, peer devices, other common network nodes, or the like and might comprise some or all of the elements described above in relation to the control server. The devices can be personal digital assistants or other like devices. Further, remote computers may be located in a variety of locations including in a medical or research environment, including clinical laboratories (e.g., molecular diagnostic laboratories), hospitals and other individual settings, ambulatory settings, medical billing and financial offices, hospital administration settings, home medical environments, and clinicians' offices. Medical providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; students; and the like. The remote computers 108 might also be physically located in nontraditional clinical environments so that the entire medical community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the database 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touchscreen, a pointing device (commonly referred to as a mouse), a trackball, or a touch pad. Other input devices comprise satellite dishes, scanners, or the like. Commands and information might also be sent directly from a remote medical device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
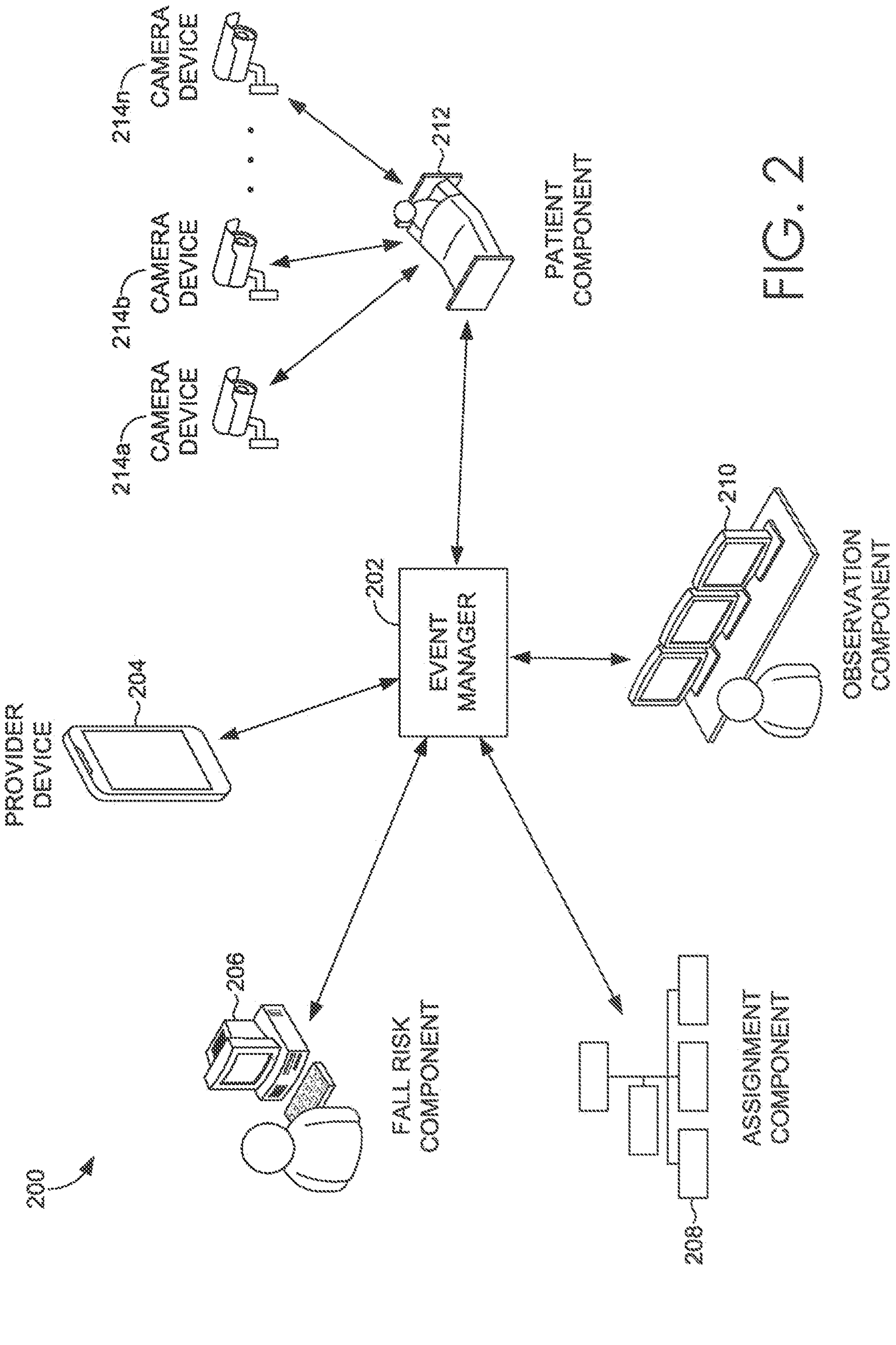
FIG. 2 depicts an exemplary framework of a virtual observation system suitable to implement embodiments of the present disclosure.

As shown in FIG. 2, an exemplary virtual observation system 200 comprises an event manager 202, a provider device 204, falls risk component 206, assignment component 208, observation component 210, patient component 212, and camera device(s) 214*a*-214*n*.

The exemplary virtual observation system 200 may be remotely located at a physical location with a data connection (e.g. USB, TCP/IP, etc.) to devices for observing a patient in real-time. The exemplary virtual observation system 200 may be on the same floor as the patient, on a different floor than the patient, in the same building as the patient, in a different building than the patient, or in a different facility than the patient. If the exemplary virtual observation system 200 is monitoring more than one patient, the patients may be located in different rooms, floors, buildings, or facilities from one another. The exemplary virtual observation system 200 may be in a single location or may be distributed amongst multiple locations.

Event manager 202 generally enables connectivity and communication between provider device 204, falls risk component 206, assignment component 208, observation component 210, patient component 212, and an EHR for the patient(s) being observed.

Provider device 204 generally receives alerts from the virtual observation system 200. The alerts may be provided to provider device(s) 204 of clinicians, a team of clinicians, or to a patient care technician (e.g., a physical sitter).

Falls risk component 206 generally enables a clinician to complete a falls risk assessment and patient safety risk assessment within the EHR of a patient. The clinician may be prompted to consider placing a camera at the bedside of the patient. Once the clinician determines the camera should be placed at the bedside of the patient, a notice is sent via the event manager 202 to observation component 210 and a provider device 204 (e.g., a technician trained to place the camera devices) that a camera needs to be placed.

Assignment component 208 generally assigns a patient to a particular clinician, team of clinicians, patient care technician, and/or virtual sitter so provider device(s) 204 corresponding to the assigned personnel can receive appropriate alerts, notifications, and patient requests, and can communicate with the patient and other assigned personnel. Assignment component 208 may be utilized to assign the location of a camera device(s) 214*a*-214*n* in the room of a patient or retrieve information corresponding to the assignment of a particular camera device(s) 214*a*-214*n* from the EHR of the patient.

Observation component 210 generally utilizes two-way camera technology to communicate with the patient via the patient component 212, communicate with a clinician or virtual sitter via provider device 204, and provides a command button panel that integrates with the EHR for documentation. A virtual sitter may be tasked to document at least once an hour. As described below, virtual guardrails can be customized for each patient. If a patient moves past the guardrail a visual cue is displayed by observation component 210 in a user interface. The virtual sitter may communicate to the patient via the camera device(s) 214*a*-214*n* and try to redirect the patient or select one of the buttons on the custom button panel (e.g., communicate an alert to and/or communicate with a clinician(s) directly).

Generally, patient component 212 streams data received from camera device(s) 214*a*-214*n* to the observation component 210 via the event manager 202. The patient component 212 may be integral to the camera device(s) 214*a*-214*n* or a distinctly separate apparatus from the camera device(s) 214*a*-214*n* possibly in a remote location from camera device(s) 214*a*-214*n* provided that the patient component 212 can receive data from the camera device(s) 214*a*-214*n*. The patient component 212 may be located in the monitored patient room, such as a hospital room or other clinical setting, bedroom, or living room. The patient component 212 may be connected to the observation component 210. The patient component and observation component 210 may be remotely located at any physical locations so long as a data connection exists (USB, TCP/IP or comparable) between the patient component 212, the observation component 210, and the camera device(s) 214*a*-214*n*.

The patient component 212 may receive data from a camera device(s) 214*a*-214*n* for a 3D zone (e.g., positioned around the patient bed or chair), a safety zone (i.e., to detect tampering with invasive line or tube placement or promote staff safety), a patient elopement zone (i.e., that provides a wide angle of a patient room to detect elopement), or a visitor monitoring zone (i.e., to prevent drug diversion and abuse). Patient component 212 may enable a virtual sitter or clinician to assign virtual guardrails to identify the boundaries of the 3D zone, the safety zone, the patient elopement zone, or the visitor monitoring zone. For example, the virtual guardrails may be assigned to a perimeter around the patient. It should be understood that the selection of a location of the virtual guardrails may vary with the individual. Virtual guardrails may be configured automatically by the patient component 212, may be configured automatically by the patient component 212 subject to confirmation and/or modification by a virtual sitter or clinician, or may be configured manually by a virtual sitter or clinician.

Camera device(s) 214*a*-214*n* generally communicates data, such as images of the patient room being monitored, to the patient component 212. The camera device(s) 214*a*-214*n* may enable two-way communication such that the patient can communicate with the virtual sitter and vice versa. Additionally, privacy mode and night vision may be provided by camera device(s) 214*a*-214*n* for patient safety. For example, in privacy mode, camera device(s) 214*a*-214*n* and/or patient component 212 may blur, pixelate, or otherwise obscure (e.g. automatically convert details of patients to cartoons, blocks, blobs, stick figures) images or videos. This may be done to protect patient privacy and modesty while still maintaining patient safety with the virtual sitter. Camera device(s) 214*a*-214*n* may be co-located with a patient room to be monitored. A patient room to be monitored may be monitored in a variety of environments, including, without limitation, a hospital, a home, a hospice care facility, a nursing home, an assisted living facility, an outpatient medical care facility, and the like.

The camera device(s) 214*a*-214*n* may be positioned where it is likely to capture images of the patient room to be monitored. For example, a camera device(s) 214*a*-214*n* may be oriented to take images of a bed, chair, or other location where a patient in the patient room to be monitored may spend a significant amount of time. In some embodiments, the camera device(s) 214*a*-214*n* may be oriented to take images of persons and/or objects entering and exiting the patient room to be monitored. In some embodiments, the camera device(s) 214*a*-214*n* may be oriented to take images of equipment (e.g., medical devices) that may be located in the patient room to be monitored.

Camera device(s) 214*a*-214*n* may capture data including 3D depth data, data defining one or more bounding boxes, skeletal object tracking data and/or blob or object tracking data. In some implementations, it may be desirable for the sensors to capture video only, or sound only, or video and sound. Alternatively, or additionally, if a virtual sitter is monitoring detailed images or video streams of patients, the data may be pixelated, or otherwise obscured (e.g. automatically convert details of patients to cartoons, blocks, blobs, stick figures). This may be done to protect patient privacy and modesty.

The camera device(s) 214*a*-214*n* may be permanently installed and activated upon an order initiated by the clinician, or may be temporarily set up in a room as needed. The patient in the patient room to be monitored may be under immediate medical care, e.g., in a medical facility under the supervision of a medical professional, or may not be under immediate care, e.g., in a clinical setting or other environment, possibly with a caregiver. A caregiver may be a medical professional or paraprofessional, such as an orderly, nurse's aide, nurse, or the like. A caregiver may also be a friend, relative, individual, company, or facility that provides assistance with daily living activities and/or medical care for individuals, such as individuals who are disabled, ill, injured, elderly, or otherwise in need of temporary or long-term assistance. In some instances, the person to be monitored may be self-sufficient and not under the immediate care of any other person or service provider.

Data associated with camera device(s) 114*a*-114*n* may be logged by observation component 210, in an EHR, or in a database. Data associated with camera device(s) 114*a*-114*n* may include, without limitation, a live image, video and/or audio feed; documentation received from a virtual sitter via the observation component 210; documentation received from a clinician via the fall risk component 206; communications provided to or received from the provider device 204 the individual(s) and/or groups to whom an alert was addressed; the response, if any, received or observed following an alert; and combinations thereof.

With reference to FIGS. 3-9, illustrative screen displays 300, 400, 500 . . . 900 of embodiments of the present invention are shown. It is understood that each of the illustrative screen displays are connected logically, such that they comprise a user interface designed for providing a virtual observation system. The screen displays may appear in any order and with any number of screen displays, without regard to whether the screen display is described or depicted herein. The screen displays may provide tools that enable utilizing a virtual observation system, in accordance with embodiments of the present invention.

Figure 3:
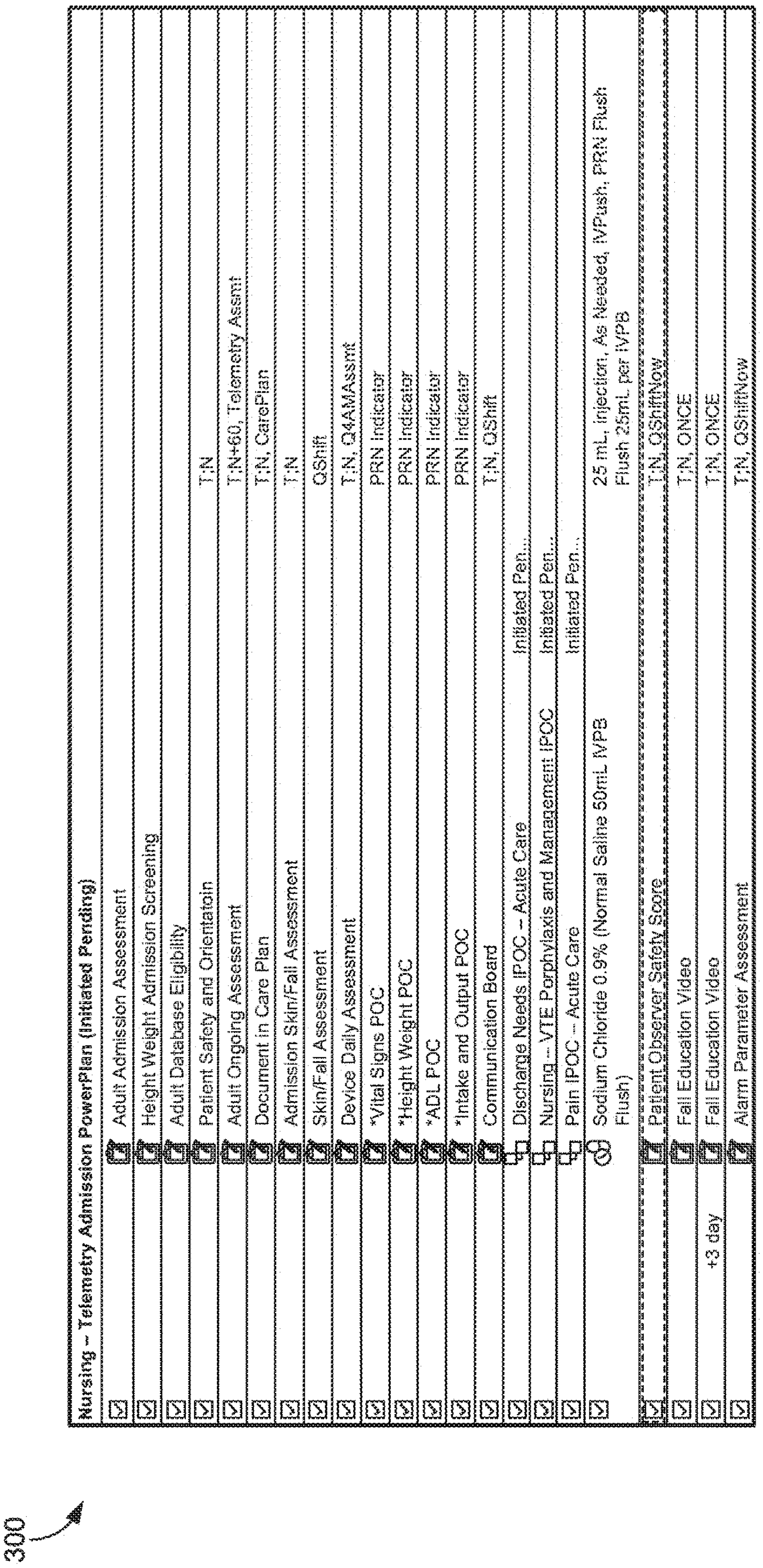
FIGS. 3-9 depict illustrative screen displays of virtual observation system, in accordance with embodiments of the present invention.

Referring initially, to FIG. 3, an admission interface 300, in one embodiment, is initially provided. The admission interface 300 enables a clinician to select an assessment for the patient. For example, the clinician may select a falls risk assessment (e.g., admission skin/fall assessment or skin/fall assessment) or a patient safety risk assessment (e.g., patient observer safety score). This enables a clinician to provide input for a falls risk assessment and/or a patient safety risk assessment that can be utilized to determine the safety assessment score for the patient. The safety assessment score is utilized to prompt the clinician to initiate an order to place a camera in the room of the patient and assign a virtual sitter to the patient.

Figure 4:
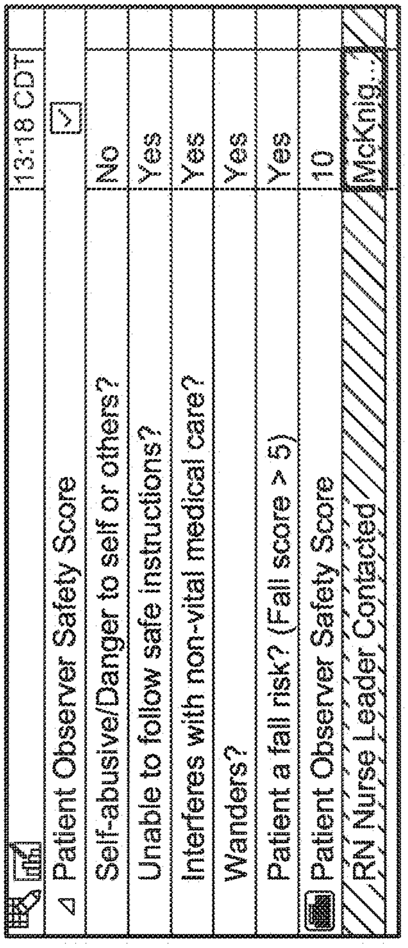

Additionally, a clinician may select, via telemetry admission interface 300, a patient observer safety score assessment. As shown in FIG. 4, selecting the patient observer safety score assessment initiates a patient observer safety score interface 400 that enables the clinician to review documentation provided by the virtual sitter. The documentation may correspond to patient behavior, initiate communication with the clinician, and/or facilitate determining whether to continue or discontinue the virtual sitter for the patient.

Figure 5:
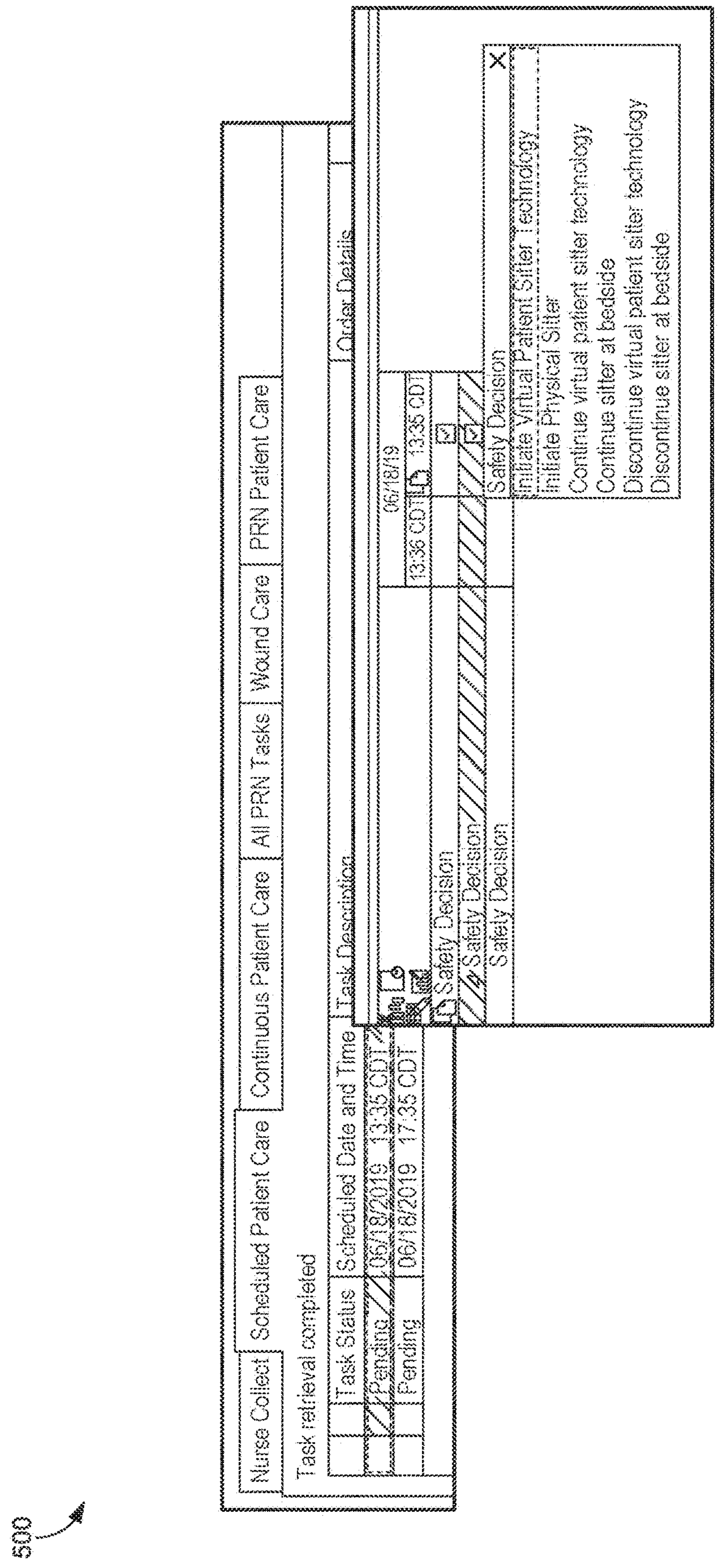

In FIG. 5, a safety decision interface 500 enables a clinician select the appropriate course of action for a patient. For example, if the safety assessment score meets a threshold, the clinician may select to initiate virtual patient sitter technology. If the safety assessment score meets a higher threshold, the clinician may select to initiate a physical sitter. Additionally, based on the documentation provided by the virtual sitter, the clinician may select to continue virtual patient sitter technology, continue sitter at bedside, discontinue virtual patient sitter technology, or discontinue sitter at bedside.

Figure 6:
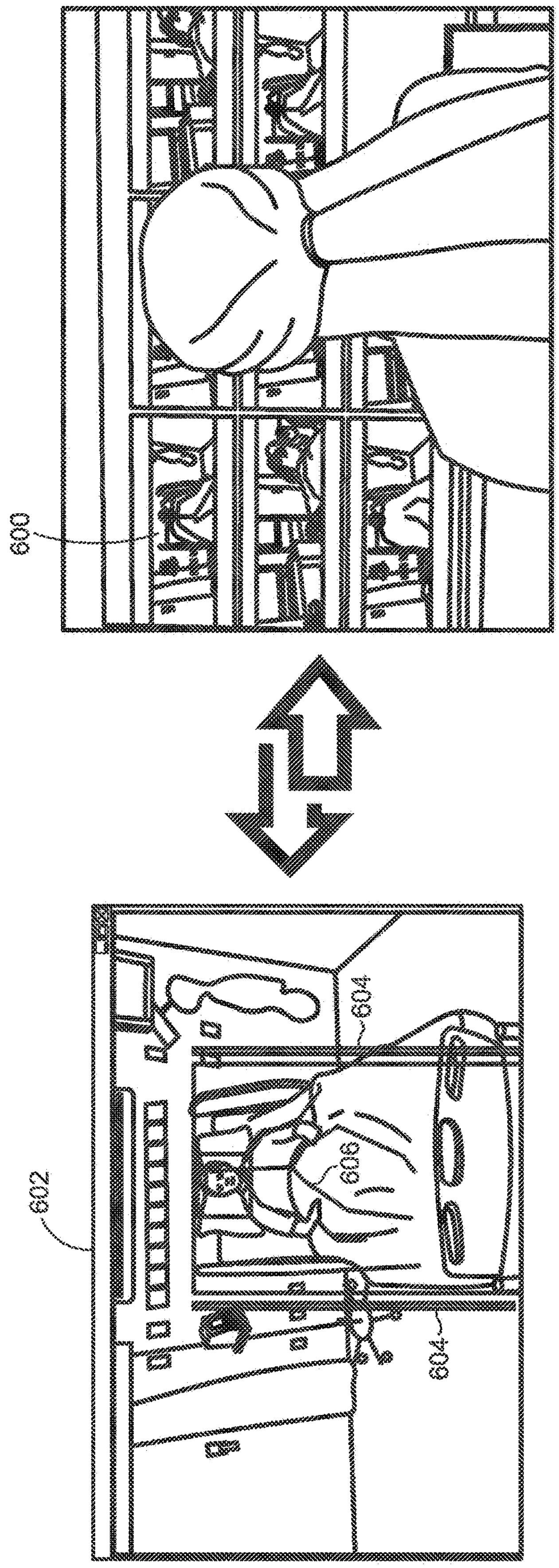

Turning now to FIG. 6, a monitoring station interface 600 enables the virtual sitter to observe up to twelve patients per monitoring station. Each patient room may have one or more camera devices to monitor the patients. A patient observation interface 602 enables the virtual sitter to focus on an individual patient. As shown in the patient observation interface 602, motion zones or virtual guardrails 604 illustrate the boundaries the patient must remain within. The patient may be tracked by the camera device(s) utilizing skeletal object tracking data (e.g., as depicted by skeleton 606). Importantly, the monitoring station interface 600 and patient observation interface 602 provide an additionally layer of care when a patient is alone in the room. Moreover, because a clinician does not need to be assigned as a physical sitter, more efficient capacity management and staffing level changes result.

Figure 7:
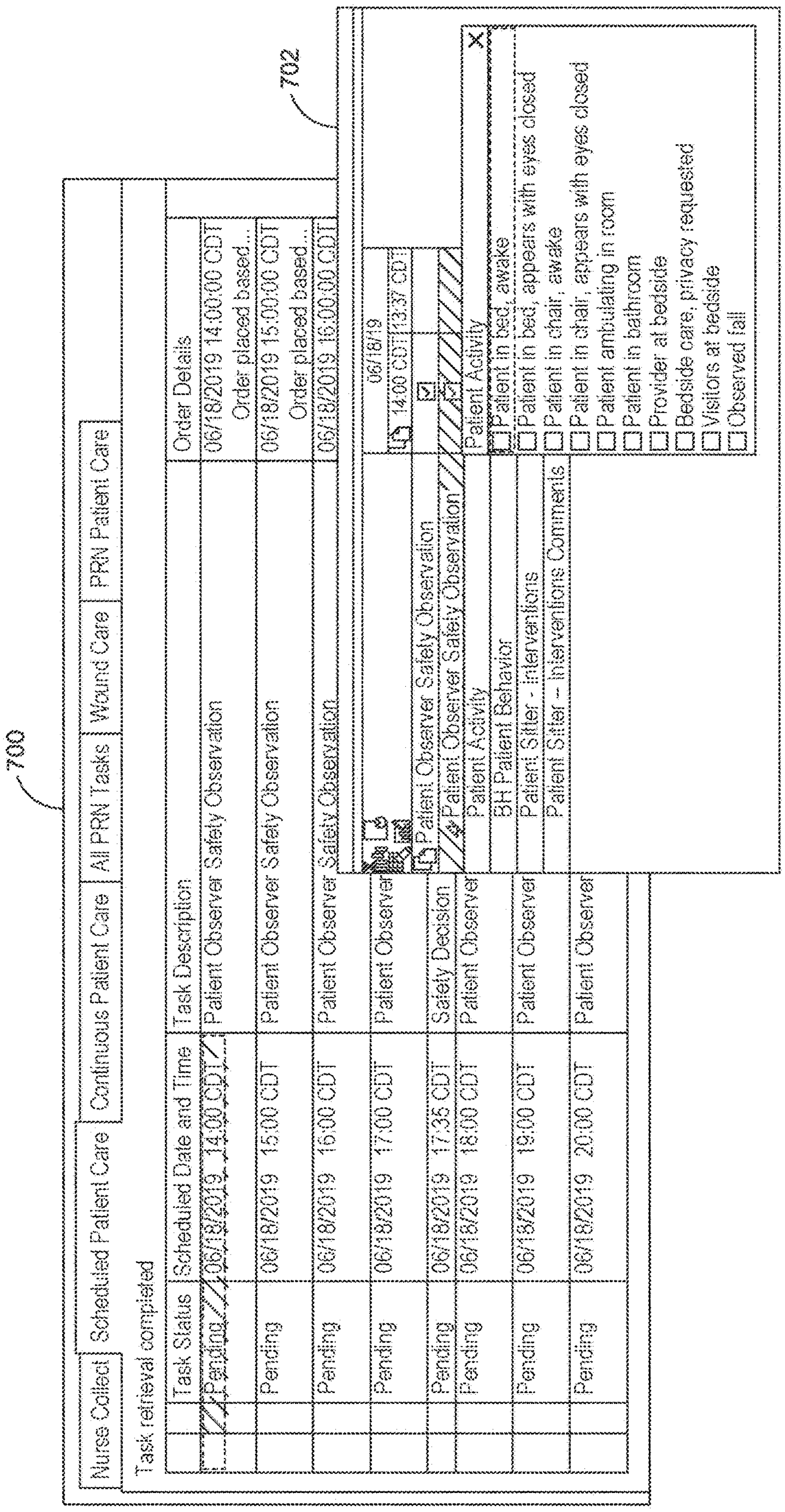

Referring to FIG. 7, an observation interface 700 illustrates the workflow for a virtual sitter. The workflow may include various tasks. Upon selection of a particular task, a safety observation interface 702 enables the virtual sitter to document various patient activities, patient behaviors, interventions, or comments corresponding the patient. For example, patient activities may indicate the patient is in bed and awake, the patient is in bed and appears to have eyes closed, the patient is in a chair and awake, the patient is in a chair and appears to have eyes closed, the patient is ambulating in the room, the patient is in the bathroom, a provider is at bedside, the patient requests privacy for bedside care, visitors are at beside, or a fall has been observed.

Figure 8:
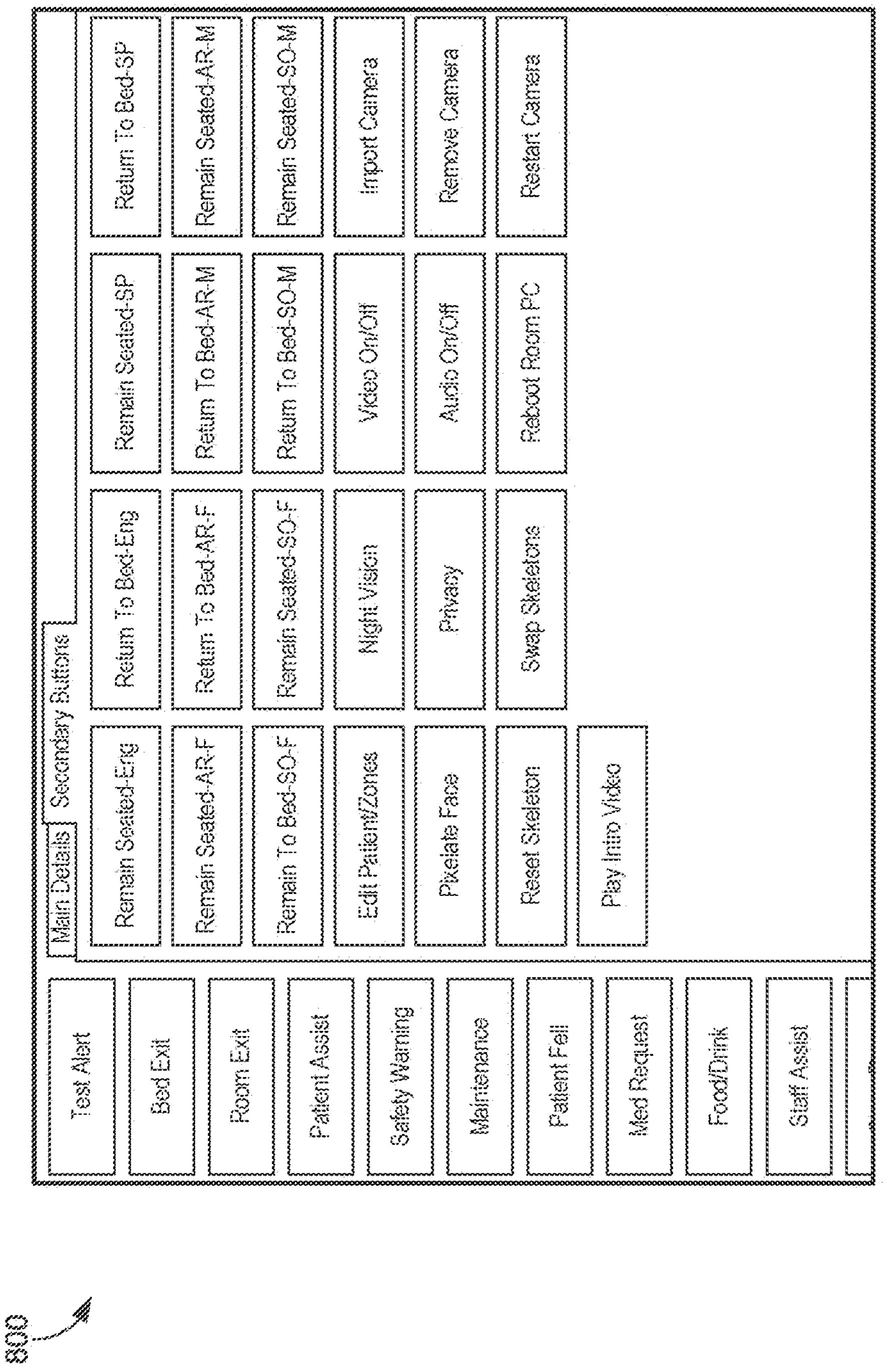

As shown in FIG. 8, a control interface 800 enables the clinical or virtual sitter to perform various functions. For example, the control interface 800 includes buttons to document patient activities, such as the patient activities described above. Additionally, the control interface 800 includes buttons to provide warnings, request medication or food and drink for the patient, request staff assistance, or perform maintenance within the virtual observation system. Maintenance may include editing the patient or the placement or location of the virtual guardrails, turning on or off various features (e.g., night vision, video, audio), pixelating features of the video such as the face of the patient, rebooting the computing device in the patient room, restarting a camera device in the patient room, importing a camera device to or removing a camera device from the patient room, or resetting or swapping skeletons (representing the patient).

Figure 9:
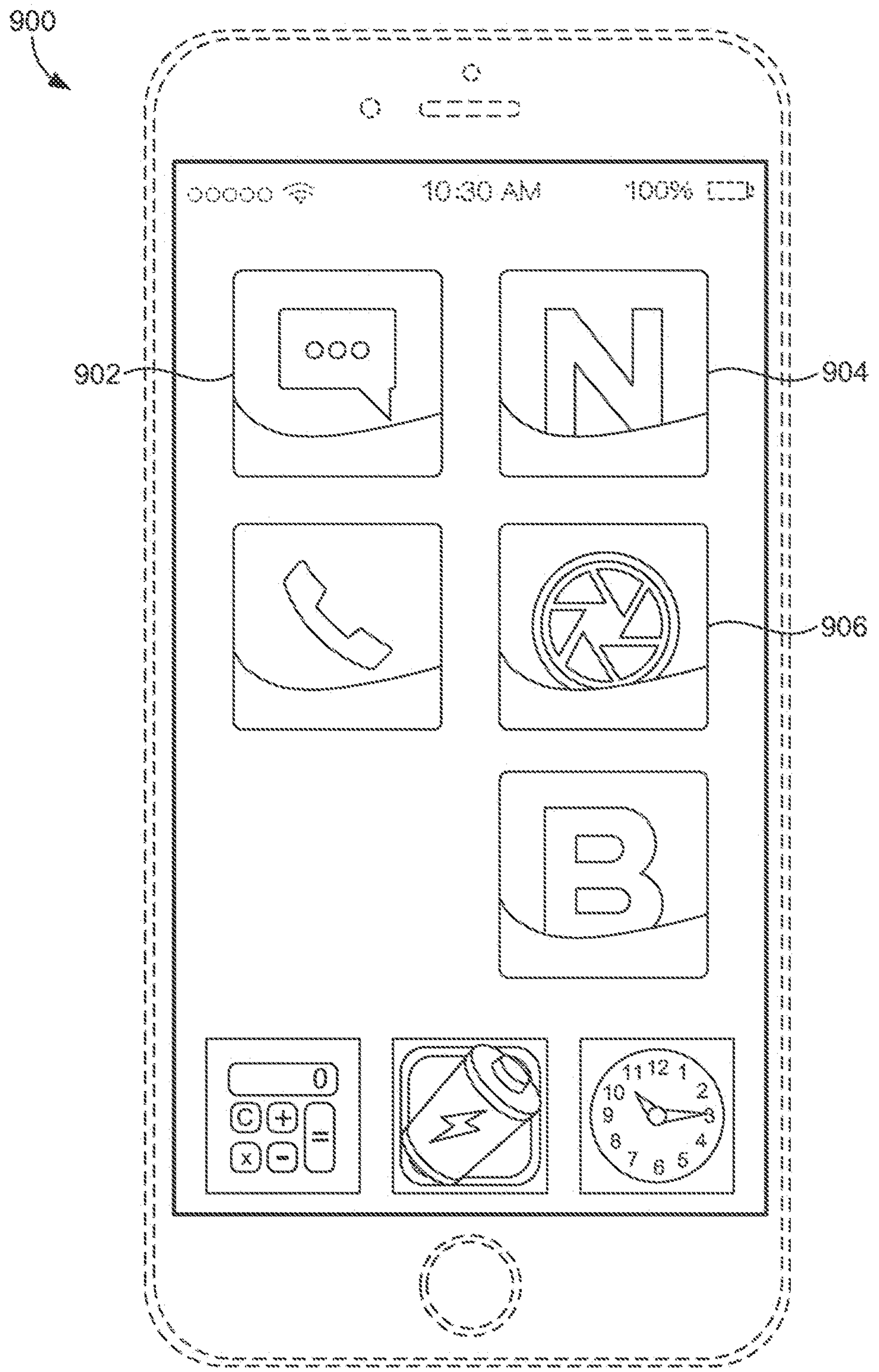

In FIG. 9, a mobile interface 900 illustrates various features that are provided to a clinician mobile device or a virtual sitter mobile device. A messenger button 902 provides a shared directory, secured text messaging, and clinical notifications and alerts (e.g., a patient is in sepsis, a patient observation is available, a medication has been prescribed). A nursing button 904 enables a clinician to review or document within an EHR for a patient (e.g., charts, orders or items, vitals, etc.), scan barcodes for administration of medications, order or review specimen collections. A camera device button 906 enables the clinician or virtual sitter to capture an image from a camera device and/or a chart for the patient.

Figure 10:
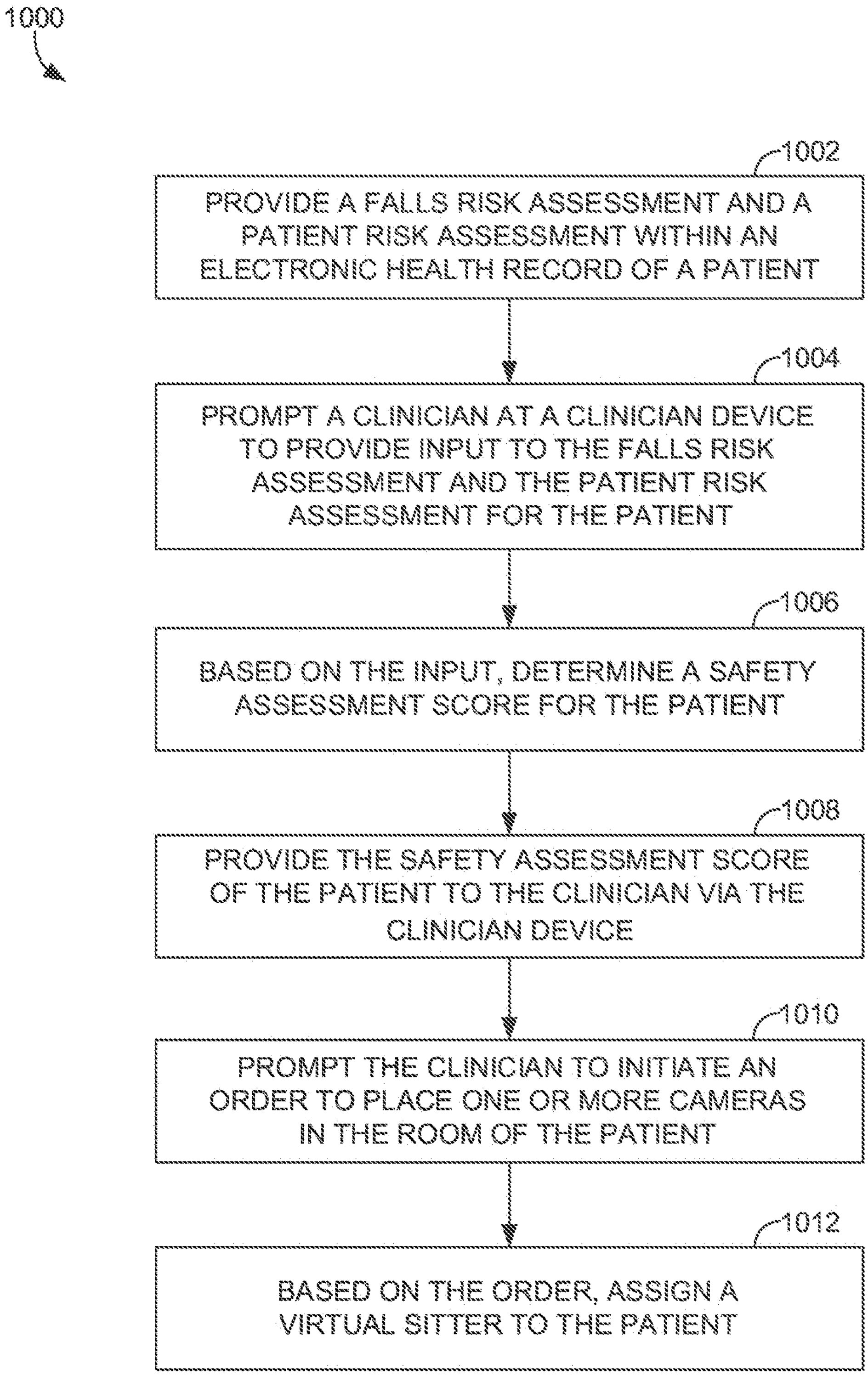
FIG. 10 is a flow diagram of a method for providing improved patient safety using virtual observation, in accordance with embodiments of the present invention.

Turning now to FIG. 10, a flow diagram is provided illustrating a method 1000 method for providing improved patient safety using virtual observation, in accordance with embodiments of the present invention. Method 1000 may be performed by any computing device (such as computing device described with respect to FIG. 1) with access to a virtual observation system (such as the one described with respect to FIG. 2) or by one or more components of the virtual observation system.

Initially, at step 1002, a falls risk assessment and a patient safety risk assessment are provided within an electronic health record of a patient. A clinician is prompted, at step 1004, to provide input via a clinician device to the falls risk assessment and the patient safety risk assessment for the patient. Based on the input, a safety assessment score is determined for the patient, at step 1006. The safety assessment score of the patient is provided, at step 1008, to the clinician via the clinician device. At step 1010, the clinician is prompted to initiate an order to place a camera in the room of the patient. Based on the order, a virtual sitter is assigned, at step 1012, to the patient.

In some embodiments, a virtual observation interface is provided. The virtual observation interface may enable the virtual sitter to communicate alerts and notifications corresponding to the patient to the clinician device, secure messages with the patient or the clinician, integrate with health care applications corresponding to the patient, and images and charts of the patient. The virtual sitter may be prompted to provide documentation at the virtual observation interface. For example, the clinician may schedule tasks at various intervals for the virtual sitter to document the patient's location within the room, behaviors of the patient, and the like. In some embodiments, the virtual observation interface enables the virtual observer to document patient activity, patient behavior, interventions, and interventions comments. Upon receiving documentation corresponding to patient activity or patient behavior, the virtual observation system may recommend or the clinician may determine whether to continue or discontinue the virtual sitter for the patient.

In some embodiments, virtual guardrails may be defined or assigned for the patient. For example, the virtual guardrails may be 3D zones positioned around a patient bed or chair. Additionally or alternatively, the virtual guardrails may be safety zones to detect tampering with invasive line or tube placement or to promote staff safety. In some embodiments, the virtual guardrails may be patient elopement zones that provide a wide angle of a patient room to detect elopement. The virtual guardrails may be visitor monitoring zones to prevent drug diversion and abuse.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A system having one or more hardware processors configured to perform a plurality of operations, the operations comprising:

receiving, at a clinician device from a virtual sitting technology management component, an instruction to present a prompt, the instruction to present the prompt received in response to a determination, at the virtual sitting technology management component and based on a machine-learning electronic model, of whether to present a falls risk assessment on the clinician device, wherein:

the machine-learning electronic model is trained by inputting, to the machine-learning electronic model, information corresponding to instances of medical information indicating patient assignment to a virtual sitter, and the determination corresponds to inputting, to the machine-learning electronic model trained on the instances, an instance of medical information associated with a patient;

presenting, by the clinician device, the prompt, wherein the prompt is configured to enable clinical input comprising falls-risk assessment information; and responsive to presenting the prompt: (a) receiving, by the clinician device, a reply corresponding to one or both of the clinical input and the falls-risk assessment information and (b) transmitting, by the clinician device, information based on the reply to the virtual sitting technology management component;

wherein the virtual sitting technology management component performs:

initiating generation of an order to assign processor based virtual sitter technology, wherein (a) the order is based on the reply and associated with activation of a processor coupled camera in a patient room and (b) a processor-based virtual sitter device is configured to electronically monitor electronic signal information associated with the camera from a location remote to the camera and electronically communicate an update associated with falls assessment information corresponding to the patient based on the monitoring;

subsequent to assignment of the processor based virtual sitter technology, electronically receiving content relating to an update for the patient, the update for the patient corresponding to the information, to the processor-based virtual sitter device, and/or to data associated with operation of the camera after the assignment of the processor based virtual sitter technology; and in response at least to receiving the content relating to the update for the patient, and based on one or both of the processor-based virtual sitter device and the data associated with the operation of the camera: (a) determining via the one or more hardware processors whether or not to continue the processor based virtual sitter technology based on the update for the patient and (b) continuing the processor based virtual sitter technology based on the update for the patient.

2. The system of claim 1, wherein training the machine-learning electronic model comprises inputting, to the machine-learning electronic model, instances of medical data indicating assignments of virtual sitters to patients.

3. The system of claim 1, wherein the operations further comprise causing storage of the falls-risk assessment information as an update in an electronic health record (EHR) of the patient.

4. The system of claim 1, wherein the operations further comprise causing the processor-based virtual sitter device to electronically monitor electronic signal information associated with the camera from a location remote to the camera based on the order.

5. The system of claim 4, wherein the processor-based virtual sitter device is configured to electronically communicate update data associated with falls assessment information corresponding to the patient based on the monitoring.

6. The system of claim 5, wherein the content relating to the update for the patient includes the update data.

7. The system of claim 1, wherein the content relating to the update for the patient is received from the processor-based virtual sitter device, and wherein the update for the patient corresponds to data associated with operation of the camera after the assignment of the processor based virtual sitter technology.

8. One or more non-transitory media having computer-readable instructions that, when executed by one or more hardware processors, cause the one or more hardware processors to perform a plurality of operations, the operations comprising:

receiving, at a clinician device from a virtual sitting technology management component, an instruction to present a prompt, the instruction to present the prompt received in response to a determination, at the virtual sitting technology management component and based on a machine-learning electronic model, of whether to present a falls risk assessment on the clinician device, wherein:

the machine-learning electronic model is trained by inputting, to the machine-learning electronic model, information corresponding to instances of medical information indicating patient assignment to a virtual sitter, and the determination corresponds to inputting, to the machine-learning electronic model trained on the instances, an instance of medical information associated with a patient;

presenting, by the clinician device, the prompt, wherein the prompt is configured to enable clinical input comprising falls-risk assessment information; and responsive to presenting the prompt: (a) receiving, by the clinician device, a reply corresponding to one or both of the clinical input and the falls-risk assessment information and (b) transmitting, by the clinician device, information based on the reply to the virtual sitting technology management component;

wherein the virtual sitting technology management component performs:

initiating generation of an order to assign processor based virtual sitter technology, wherein (a) the order is based on the reply and associated with activation of a processor coupled camera in a patient room and (b) a processor-based virtual sitter device is configured to electronically monitor electronic signal information associated with the camera from a location remote to the camera and electronically communicate an update associated with falls assessment information corresponding to the patient based on the monitoring;

subsequent to assignment of the processor based virtual sitter technology, electronically receiving content relating to an update for the patient, the update for the patient corresponding to the information, to the processor-based virtual sitter device, and/or to data associated with operation of the camera after the assignment of the processor based virtual sitter technology; and in response at least to receiving the content relating to the update for the patient, and based on one or both of the processor-based virtual sitter device and the data associated with the operation of the camera: (a) determining via the one or more hardware processors whether or not to continue the processor based virtual sitter technology based on the update for the patient and (b) continuing the processor based virtual sitter technology based on the update for the patient.

9. The one or more non-transitory media of claim 8, wherein training the machine-learning electronic model comprises inputting, to the machine-learning electronic model, instances of medical data indicating assignments of virtual sitters to patients.

10. The one or more non-transitory media of claim 8, wherein the operations further comprise causing storage of the falls-risk assessment information as an update in an electronic health record (EHR) of the patient.

11. The one or more non-transitory media of claim 8, wherein the operations further comprise causing the processor-based virtual sitter device to electronically monitor electronic signal information associated with the camera from a location remote to the camera based on the order.

12. The one or more non-transitory media of claim 11, wherein the processor-based virtual sitter device is configured to electronically communicate update data associated with falls assessment information corresponding to the patient based on the monitoring.

13. The one or more non-transitory media of claim 12, wherein the content relating to the update for the patient includes the update data.

14. The one or more non-transitory media of claim 8, wherein the content relating to the update for the patient is received from the processor-based virtual sitter device, and wherein the update for the patient corresponds to data associated with operation of the camera after the assignment of the processor based virtual sitter technology.

15. A computer-implemented method, performed by one or more hardware processors, the computer-implemented method comprising:

receiving, at a clinician device from a virtual sitting technology management component, an instruction to present a prompt, the instruction to present the prompt received in response to a determination, at the virtual sitting technology management component and based on a machine-learning electronic model, of whether to present a falls risk assessment on the clinician device, wherein:

the machine-learning electronic model is trained by inputting, to the machine-learning electronic model, information corresponding to instances of medical information indicating patient assignment to a virtual sitter, and the determination corresponds to inputting, to the machine-learning electronic model trained on the instances, an instance of medical information associated with a patient;

presenting, by the clinician device, the prompt, wherein the prompt is configured to enable clinical input comprising falls-risk assessment information; and responsive to presenting the prompt: (a) receiving, by the clinician device, a reply corresponding to one or both of the clinical input and the falls-risk assessment information and (b) transmitting, by the clinician device, information based on the reply to the virtual sitting technology management component;

wherein the virtual sitting technology management component performs:

initiating generation of an order to assign processor based virtual sitter technology, wherein (a) the order is based on the reply and associated with activation of a processor coupled camera in a patient room and (b) a processor-based virtual sitter device is configured to electronically monitor electronic signal information associated with the camera from a location remote to the camera and electronically communicate an update associated with falls assessment information corresponding to the patient based on the monitoring;

subsequent to assignment of the processor based virtual sitter technology, electronically receiving content relating to an update for the patient, the update for the patient corresponding to the information, to the processor-based virtual sitter device, and/or to data associated with operation of the camera after the assignment of the processor based virtual sitter technology; and in response at least to receiving the content relating to the update for the patient, and based on one or both of the processor-based virtual sitter device and the data associated with the operation of the camera: (a) determining via the one or more hardware processors whether or not to continue the processor based virtual sitter technology based on the update for the patient and (b) continuing the processor based virtual sitter technology based on the update for the patient.

16. The computer-implemented method of claim 15, wherein training the machine-learning electronic model comprises inputting, to the machine-learning electronic model, instances of medical data indicating assignments of virtual sitters to patients.

17. The computer-implemented method of claim 15, further comprising causing storage of the falls-risk assessment information as an update in an electronic health record (EHR) of the patient.

18. The computer-implemented method of claim 15, further comprising causing the processor-based virtual sitter device to electronically monitor electronic signal information associated with the camera from a location remote to the camera based on the order.

19. The computer-implemented method of claim 18, wherein the processor-based virtual sitter device is configured to electronically communicate update data associated with falls assessment information corresponding to the patient based on the monitoring.

20. The computer-implemented method of claim 15, wherein the content relating to the update for the patient is received from the processor-based virtual sitter device, and wherein the update for the patient corresponds to data associated with operation of the camera after the assignment of the processor based virtual sitter technology.

* * * * *